(12) United States Patent
Bonrath et al.

(10) Patent No.: US 8,198,443 B2
(45) Date of Patent: Jun. 12, 2012

(54) SYNTHESIS OF 4-AMINO-PYRIMIDINES SCAFFOLDS

(75) Inventors: Werner Bonrath, Freiburg (DE); Ralph Haerter, Biel-Benken (CH); Reinhard Karge, Staufen (DE); Ulla Letinois, Saint-Louis (FR)

(73) Assignee: DSM IP Assets B.V., Heerlen (NL)

( * ) Notice: Subject to any disclaimer, the term of this patent is extended or adjusted under 35 U.S.C. 154(b) by 275 days.

(21) Appl. No.: 12/522,929

(22) PCT Filed: Jan. 7, 2008

(86) PCT No.: PCT/EP2008/000320
§ 371 (c)(1),
(2), (4) Date: Jul. 13, 2009

(87) PCT Pub. No.: WO2008/087021
PCT Pub. Date: Jul. 24, 2008

(65) Prior Publication Data
US 2010/0016591 A1      Jan. 21, 2010

(30) Foreign Application Priority Data
Jan. 19, 2007  (EP) .................................... 07001136

(51) Int. Cl.
*C07D 239/02*      (2006.01)
(52) U.S. Cl. ........................ 544/329; 544/326
(58) Field of Classification Search .................. 544/326, 544/329
See application file for complete search history.

(56) References Cited

U.S. PATENT DOCUMENTS 3,855,359 A * 12/1974 Weil .............................. 558/164
4,942,085 A *  7/1990 Guerro et al. ................. 442/85
5,140,047 A *  8/1992 Adams et al. ................. 514/575
5,461,075 A * 10/1995 O'Neill et al. ................ 514/617

FOREIGN PATENT DOCUMENTS
DE        35 11 273      10/1986

OTHER PUBLICATIONS

J. March, Advanced Organic Chemistry Reactions, Mechanisms and Structure 37-64, 334-229 (3rd ed., 1985).*
Hawley'S Condensed Chemical Dictionary 38-1107 (R.J. Lewis, Sr. ed., 15th ed., 2007).*
R.G. Perrin, Journal of the American Chemical Society, 85, 3533-3539 (1963).*
The Condensed Chemical Dictionary 822 (Gessner G. Hawley ed., 9th ed., 1977).*
Concise Chemical and Technical Dictionary 1081 (H. Bennett ed., 4th ed., 1986).*
Hawley'S Condensed Chemical Dictionary 1186 (Richard J. Lewis, Sr. ed., 15th ed., 2007).*
D.D. Perin et al., Purification of Laboratory Chemicals 235-236 (2nd ed., 1980).*
Reichardt, Solvents and Solvent Effects in Organic Chemistry (3rd ed., 2003).*
J. Leonard et al., Advanced Practical Organic Chemistry 128-176, 129 (2nd ed., 1985).*
Ming-Ii et al, Yingyong Huagong, 34(8), 513-514 (2005).*
International Search Report for PCT/EP2008/000320, mailed May 26, 2008.

* cited by examiner

*Primary Examiner* — James O Wilson
*Assistant Examiner* — Alexander R Pagano
(74) *Attorney, Agent, or Firm* — Nixon & Vanderhye P.C.

(57) ABSTRACT

Process for the manufacture of a compound of the structure (I) with $R^1$=hydrogen, alkyl (C1-C10, linear, cyclic or branched, aliphatic or aromatic), NR'R" (wherein R' and R" are independently selected from H, alkyl [C1-C10, linear, cyclic or branched, aliphatic or aromatic] and $R^2=CH_2R^3$ wherein $R^3$ is selected from NHR1''' (with R'''=C(O)H, C(O)CH$_3$, C(O) alkyl, $CH_2C_6H_2(OMe)_3$ or other saponifiable residues), alkyl (C1-C10, linear, cyclic or branched) aromatic residues, heteroaryl residues, substituted aryl residues, e.g. 3,4,5-trimethoxy-phenyl) wherein 1 equivalent of an α-formyl-propionitrile salt is reacted with 0.75 to 2 equivalents of an acetamidine salt in the presence of a Lewis acid.

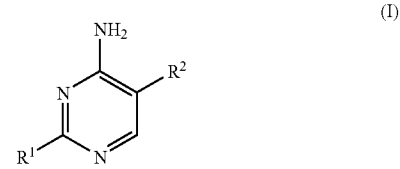

(I)

23 Claims, No Drawings

SYNTHESIS OF 4-AMINO-PYRIMIDINES SCAFFOLDS

This application is the U.S. national phase of International Application No. PCT/EP2008/000320, filed 17 Jan. 2008, which designated the U.S. and claims priority to Europe Application No. 07001136.6, filed 19 Jan. 2007, the entire contents of each of which are hereby incorporated by reference.

The present invention relates to the direct transformation of an α-formyl-propionitrile salt (Li-, Na- or K-salt) to substituted 4-amino-pyrimidines. In particular it relates to a new reaction to 2-methyl-4-amino-5-formylaminomethylpyrimidine by a cyclization reaction of an α-formyl-β-formylaminopropionitrile salt (Li-, Na- or K-salt) and acetamidine hydrochloride.

Importance of 4-aminopyrimidines 4-aminopyrimidines and the aminosubstituted derivatives can be found as structural elements in several antibiotic substances, in herbicides as well as in vitamin B1.

For example trimethoprim is a bacteriostatic antibiotic mainly used in the prophylaxis and treatment of urinary tract infections. It belongs to the class of chemotherapeutic agents known as dihydrofolate reductase inhibitors. Trimethoprim was formerly marketed by GlaxoWellcome under trade names including Proloprim®, Monotrim® and Triprim®.

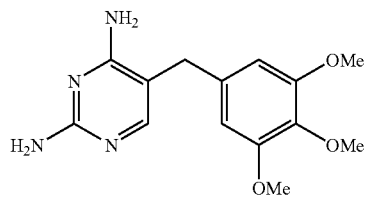

Amprolium (sold as CORID®), thiamine analog, competitively inhibits the active transport of thiamine. The coccidia are 50 times as sensitive to this inhibition as is the host. It can prevent costly coccidial infection in exposed cattle and treat clinical outbreaks when they do occur. By stopping coccidia in the small intestine, CORID® prevents more damaging coccidiosis in the large intestine.

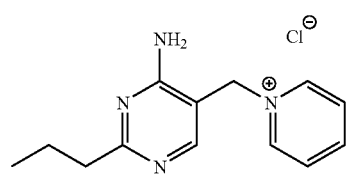

Importance of 4-amino-5-aminomethyl-2-methylpyrimidine 4-amino-5-aminomethyl-2-methylpyrimidine is an important intermediate in the synthesis of vitamin $B_1$. Vitamin B1 (thiamin) is used chiefly in the form of chloride hydrochloride (1) and nitrate.

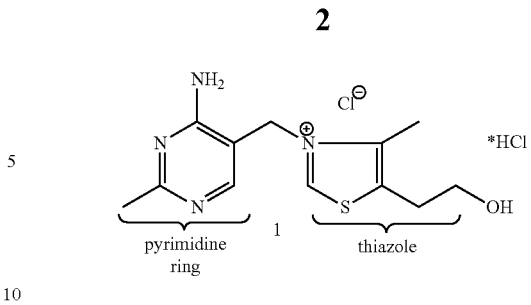

It is widespread in nature, for example 2.05 mg/100 g wheat germ, 1.3 mg/100 g in soybeans. A deficiency in vitamin $B_1$ in the human being is associated with the disease beriberi, with imbalances in carbohydrate status and deleterious effects on nerve functions. A human being needs 20-30 μg/kg body weight, which corresponds to 0.3-1.5 mg/d daily allowance. Since extraction of thiamin from natural sources would not be economically profitable, it has to be manufactured by chemical synthesis. Industrial production of vitamin $B_1$ started in 1937 by Hoffmann-La Roche in Switzerland and Merck in the United States. Commercially available forms of thiamin are the chloride hydrochloride and the mononitrate.

4-amino-5-aminomethyl-2-methylpyrimidine is a key-intermediate in the synthesis of thiamin which contains a thiazole and a pyrimidine ring. One main approach towards the synthesis of thiamin is the pyrimidine synthesis and subsequent formation of the thiazole ring attached to the pyrimidine moiety from 4-amino-5-aminomethyl-2-methylpyrimidine and 3-chloro-5-hydroxy-pentan-2-one, the 3-mercaptoketone or the corresponding acetates. Several procedures have been published for the synthesis of 4-amino-5-aminomethyl-2-methylpyrimidine. The building blocks are based on a C2-unit, e.g. acetamidine, and a C1-unit, usually from CO. Acrylonitrile can be used as C2-unit as a cheap starting material for the synthesis.

STATE OF THE ART

JP 39022009 and JP 39022010 describe the synthesis of 2-methyl-4-amino-5-formylamino-methylpyrimidine by reacting formamidine hydrochloride with sodium and ethanol to liberate the amidine followed by an addition of 2-(ethoxymethoxymethyl)-3-ethoxypropionitrile. This procedure is disadvantageous as it necessitates an extra reaction step, the liberation of form-amidine from the hydrochloride and the synthesis of the enol ethyl ether.

The UBE-Takeda procedure for over seven steps [EP-055 108-A1; EP-279 556-A1; DE-33 03 815-A1; EP-124 780-A1; EP-290 888-A2; DE-32 22 519-A1] includes in the first step the transformation of acrylonitrile to cyanoacetaldehyde-dimethylacetal. This step is very complex and requires major investigations because the oxidation of acrylonitrile with methyl nitrite leads to the formation of nitrous gases which have to be reoxidized to nitrite [EP-055 108-A1].

The UBE-approach over 5 steps [DE-32 18 068-A1, JP-58065262] needs two equivalents of acetamidine hydrochloride. Acetamidine hydrochloride is expensive; therefore it is disadvantageous to use two equivalents as starting material.

The 5 step procedure from BASF [EP-172 515-A1] uses o-chloroaniline for the synthesis of the corresponding enamine. o-Chloroaniline is suspected to provoke cancer. The enamine is used in the following step for the cyclization with acetamidine. After the formation of 4-amino-5-aminomethyl-2-methylpyrimidine the o-chloroaniline has to be separated and re-used in a complex process.

In the presence of ammonia acrylonitrile reacts to amino-propionitrile (APN). APN is a commercially interesting intermediate, e.g. as it is useful as starting material for both the synthesis of vitamin $B_1$ as well as the synthesis of calcium pantothenate.

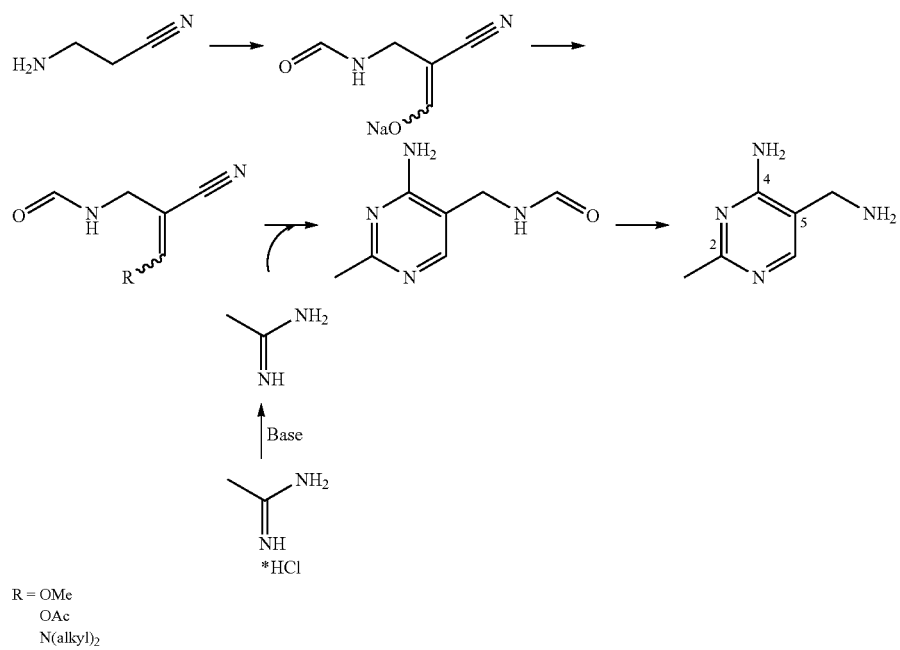

R = OMe
OAc
N(alkyl)₂

The key-step in this approach is the cyclization of derivatives of α-formyl-β-formylaminopropio-nitrile sodium salt with acetamidine. These derivatives can be for example the enamines, acetates or methylenolethers of α-formyl-β-formylaminopropionitrile sodium salt [see for example EP-001 760-A2, DE-28 18 156-A1, DE-23 23 845]. For the cyclization reaction between α-formyl-β-formylaminopropionitrile sodium salt and acetamidine, the acetamidine has to be liberated from its hydrochloride. Severe drawbacks of this procedure are the formation of a salt, additional costs for the base and additional reaction steps including work-up, e.g. by filtration of the salts.

The patent application DE-35 11 273-A1 describes the direct cyclization of α-formyl-β-formyl-aminopropionitrile sodium salt with acetamidine hydrochloride with neither having to derivatize any of the mentioned starting materials nor having to liberate the acetamidine from its hydrochloride:

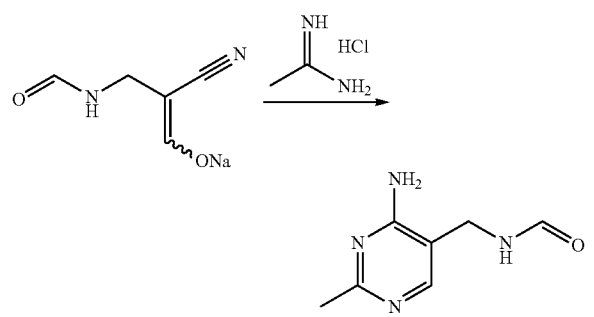

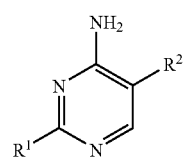

The process consists of reacting α-formyl-β-formylaminopropionitrile sodium salt having a minimal purity of 92% with acetamidine hydrochloride in a solvent like isopropanol, methylisobutylcarbinol, open chain- or cyclic ethers during 4 to 6 hours at reflux yielding 2-methyl-4-amino-5-formylaminomethylpyrimidine and subsequent hydrolysis leading to 4-amino-5-aminomethyl-2-methylpyrimidine. The reported yield is 57%. Unfortunately it was not possible to obtain the reported yield under the reported conditions. The highest yield obtainable under the reported conditions was in fact 35%.

Main disadvantages of the process described in the DE-35 11 273-A1 for an industrial scale application are the poor yield—which makes the process economically unattractive—and the fact that the starting materials have to have a minimal purity of 92%. In addition to that, only the hydrochloride of the acetamidine can be used.

It was therefore an object of the following invention to provide a new way to 4-amino-5-aminomethyl-2-methylpyrimidine—preferably over a maximum of four steps—which allows a considerable yield improvement and most preferred without using highly toxic reagents—like dimethylsulfate or o-chloro aniline.

It has surprisingly been found that the object of the present invention is achieved by a process for the manufacture of a compound of the structure with
$R^1$=hydrogen, alkyl (C1-C10, linear, cyclic or branched, aliphatic or aromatic), NR'R'' (wherein R' and R'' are independently selected from H, alkyl [C1-C10, linear, cyclic or branched, aliphatic or aromatic] and
$R^2$=CH₂R³ wherein R³ is selected from NHR''' (with R'''=C(O)H, C(O)CH₃, C(O)alkyl, CH₂C₆H₂(OMe)₃ or other saponifiable residues), alkyl (C1-C10, linear, cyclic or branched) aromatic residues, heteroaryl residues, substituted aryl residues, e.g. 3,4,5-trimethoxy-phenyl)

wherein 1 equivalent of an α-formyl-propionitrile salt is reacted with 0.75 to 2 equivalents of an acetamidine salt in the presence of a Lewis acid at the following reaction conditions:
a. a reaction temperature of 65 to 200 C;
b. a pressure of 1 to 10 bar;
c. a reaction time of 0.5 to 20 hours;
d. a concentration 1-50 wt % α-formylpropionitrile salt in the corresponding solvent;
e. stirring between 100 and 900 rps;
f. under air or nitrogen or argon or mixtures thereof.

The starting materials can be added in any order to the reaction vessel.

It was not to be foreseen by the person skilled in the art that Lewis acids would enhance the reactivity of α-formylpropionitrile salt towards the desired substituted 4-amino-pyrimidine.

It was also surprising for the skilled person that the purity of the α-formyl-propionitrile salt is of less importance for the result of the process according to the present invention and can accordingly be chosen from 30% to 100%.

Furthermore various acetamidine salts can be used as starting material. Preferred are acetamidine salts of acids that have a $pK_a$ value below 5; especially preferred are acetamidine hydrochloride, acetamidine hydrobromide, acetamidine acetate, most preferred is acetamidine hydrochloride.

In a preferred embodiment of the present invention an α-formyl-β-formylaminopropionitrile salt (Li-, Na- or K-salt) is reacted with an acetamidine salt to 2-methyl-4-amino-5-formylamino-methylpyrimidine.

One advantage of the process according to the present invention is that in an especially preferred embodiment purification is not necessary: 2-methyl-4-amino-5-formylaminomethyl-pyrimidine can be purified as described in patent application WO 2006/079504 A2, i.e. after the hydrolysis of 2-methyl-4-amino-5-formylaminomethylpyrimidine to 4-amino-5-aminomethyl-2-methylpyrimidine an easy liquid/liquid purification of the crude reaction mixture is carried out to obtain 4-amino-5-aminomethyl-2-methylpyrimidine in high yield and high purity.

In an especially preferred embodiment the process of the present invention therefore preferably comprises the following additional step(s):
i) hydrolysis of the 2-methyl-4-amino-5-formylaminomethylpyrimidine to 4-amino-5-aminomethyl-2-methylpyrimidine;
ii) phase separating the reaction mixture in an aqueous and an organic phase;
iii) optionally extracting the aqueous phase with the organic solvent (mixture) used in the previous steps and combining the organic phases.

Steps i) to iii) may be performed in any way known to the person skilled in the art.

According to the present invention it is preferred to react 1 equivalent of an α-formyl-β-formyl-aminopropionitrile salt with 1 to 1.8 equivalents of acetamidine salt, more preferred with 1.1 to 1.3 equivalents of acetamidine salt.

In preferred embodiments of the present invention the Lewis acids (one or more compounds) are selected from salts of alkaline earth metals (especially Be, Mg, Ca), transition metals (especially Fe, Co, Ni, Ru, Rh, Pd, Cu, Ag, Au, Zn), poor metals (especially Al, Ga, In) and/or lanthanides; preferred are salts of transition metals; especially preferred are iron (II)-, cobalt(II)-, ruthenium(II)-, copper(I) and/or zinc (II) salts.

Examples of especially preferred Lewis acids are: $ZnCl_2$, $ZnBr_2$, $Zn((SO_2C_nF_{2n+1})_2)N)_2$ with n=1 to 8, $FeCl_2$, $CoCl_2$, $Ru(COD)Cl_2$ (wherein COD=1,5-cyclooctadiene), CuCl; most preferred are CuCl, $FeCl_2$ and $ZnCl_2$.

According to the present invention it can be advantageous to use further additives which e.g. further enhance the yield of the desired product. Examples of such additives are $MgSO_4$ and/or $NaSO_4$.

It is further preferred to use solvents or mixtures of solvents which do not have a primary alcohol function, like hydrocarbons, aromatic compounds, ethers, ketones, esters, carbonates, alkohols, tertiary amines, nitrites, amides, acetonitrile and so on. Preferred are aromatic compounds, ketones, carbonates, tertiary amines or any mixtures of these solvents; especially preferred are 3-pentanone, triethylamine and/or toluene or any mixtures of these solvents. 3-pentanone is most preferred.

An example of a preferred mixture of solvents is a mixture of 3-pentanone and isopropanol in a volume ratio of from 9:1 to 1:9, preferred in a volume ratio of from 8:2 to 2:8, especially preferred in a volume ratio of from 7.5:2.5 to 6:4.

According to the present invention traces of water and/or another polar solvent can be advantageous. It is preferred if the amount of water and/or another polar solvent is in the range of 0.005 to 1 equivalents, more preferred in the range of 0.05 to 0.5 equivalents.

According to the present invention it is advantageous to adjust the reaction conditions as follows:
  a reaction temperature in the range of 70 to 150 C preferred of 80 to 150 C more preferred of 85 to 120 C
  a pressure in the range of 1 to 10 bar, preferred of 1 to 6 bar;
  a reaction time in the range of 0.5 to 20 hours, preferred of 1 to 10 hours, more preferred of 2.5 to 4 hours;
  under protective atmosphere.

The invention is further illustrated by the following examples.

EXAMPLES

Example 1

In the Presence of $ZnBr_2$ 1 g of α-formyl-β-formylaminopropionitrile sodium salt (84%, 5.7 mmol) were placed in a three-necked, round bottom 25 mL flask, fitted with a reflux-condenser, a magnetic stirrer and an argon supply. Acetamidine hydrochloride (638 mg, 6.8 mmol, 1.19 eq.), $ZnBr_2$ (398 mg, 0.3 eq.) and finally 5.4 mL of 3-pentanone were added.

The mixture was stirred at 300 rpm under argon at 90° C. (internal temperature) for 24 h. After 18 minutes solids became brown and sticky, stirring was not possible anymore. After 24 hours, the solvent was removed at reduced pressure at 40° C. (10 mbar) and the reaction mixture was analyzed by HPLC and NMR. The yield was 74% based on α-formyl-β-formylaminopropionitrile sodium salt.

NMR spectra were recorded on a Bruker Avance 300 MHz spectrometer. $^1$H-NMR were recorded at 300 MHz, $^{13}$C spectra were recorded at 75 MHz, respectively. The quantitative spectra were recorded in DMSO-$d_6$ using p-dimethoxyhydroquinone as internal standard. The delay between two pulses was set to 30 s. 12-25 mg samples were used.

Example 2

In the Presence of $ZnCl_2$ 100 g α-formyl-β-formylaminopropionitrile sodium salt: (82%, 552 mmol) were placed in a three-necked, round bottom 500 mL flask, fitted with a reflux-condenser, a magnetic stirrer and an argon supply. Acetamidine hydrochloride (64.5 g, 662 mmol, 1.20 eq.), $ZnCl_2$ (19.9 g, 0.26 eq.) and finally 300 mL of 3-pentanone were added.

The mixture was stirred at 300 rpm under argon at 90° C. (internal temperature) for 19 h. After 19 hours, the solvent was evaporated at reduced pressure at 40° C. (10 mbar) and the reaction mixture was analyzed by HPLC and NMR. The yield in the crude reaction mixture was 74% based on α-formyl-β-formylaminopropionitrile sodium salt.

Example 3

In the Presence of $CoCl_2$ 1 g of α-formyl-β-formylaminopropionitrile sodium salt (80.5%, 5.4 mmol) were placed in a three-necked, round bottom 25 mL flask, fitted with a reflux-condenser, a magnetic stirrer and an argon supply. Acetamidine hydrochloride (640 mg, 6.5 mmol, 1.2 eq.), $CoCl_2$ (1.40 g, 0.2 eq.) and finally 5 mL of 3-pentanone were added.

The mixture was stirred at 300 rpm under argon at 90° C. (internal temperature). After 18 hours, the solvent was removed at reduced pressure at 40° C. (10 mbar) and the reaction mixture was analyzed by HPLC and NMR. The yield of the pyrimidine in the crude reaction mixture was 72% based on α-formyl-β-formylaminopropionitrile sodium salt.

Example 4

In the Presence of $ZnCl_2$ 1 g of α-formyl-β-formylaminopropionitrile sodium salt (80.5%, 5.4 mmol) were placed in a 20 mL Carius tube fitted with a magnetic stirrer. Acetamidine hydrochloride (652 mg, 6.5 mmol, 1.28 eq.), $ZnCl_2$ (165 mg, 0.22 eq.) and finally 3.5 mL of 3-pentanone and 2 mL of isopropanol were added.

The mixture was stirred at 300 rpm under argon at 90° C. (bath temperature). After 18 hours, the solvent was evaporated at reduced pressure at 40° C. (10 mbar) and the reaction mixture was analyzed by HPLC and NMR. The yield of the pyrimidine in the crude reaction mixture was 71% based on α-formyl-β-formylaminopropionitrile sodium salt.

Example 5

In the Presence of $FeCl_2$ 1 g of α-formyl-β-formylaminopropionitrile sodium salt (77%, 5.2 mmol) were placed in a three-necked, round bottom 25 mL flask, fitted with a reflux-condenser, a magnetic stirrer and an argon supply. Acetamidine hydrochloride (506 mg, 5.2 mmol, 1 eq.), $FeCl_2$ (170 mg, 0.26 eq.) and finally 3 mL of 3-pentanone were added.

The mixture was stirred at 500 rpm under argon at 90° C. (internal temperature). After 18 hours, the solvent was removed at reduced pressure at 40° C. (10 mbar) and the reaction mixture was analyzed by HPLC and NMR. The yield of the pyrimidine in the crude reaction mixture was 63% based on α-formyl-β-formylaminopropionitrile sodium salt.

Example 6

In the Presence of $FeCl_2$ 5 g of α-formyl-β-formylaminopropionitrile sodium salt (77%, 26 mmol) were placed in a three-necked, round bottom 50 mL flask, fitted with a reflux-condenser, a magnetic stirrer and an argon supply. Acetamidine hydrochloride (2.91 g, 29.9 mmol, 1.15 eq.), $FeCl_2$ (703 mg, 0.21 eq.) and finally 15 mL of t-butanol were added.

The mixture was stirred at 300 rpm under argon at 90° C. (internal temperature). After 18 hours, the solvent was evaporated at reduced pressure at 40° C. (10 mbar) and the crude reaction mixture was analyzed by HPLC and NMR. The yield of the pyrimidine in the crude reaction mixture was 59% based on α-formyl-β-formylaminopropionitrile sodium salt.

Example 7

In the Presence of $Ru(COD)Cl_2$ 1 g of α-formyl-β-formylaminopropionitrile sodium salt (80.5%, 5.4 mmol) were placed in a three-necked, round-bottom 25 mL flask, fitted with a reflux-condenser, a magnetic stirrer and an argon supply. Acetamidine hydrochloride (633 mg, 6.5 mmol, 1.2 eq.), $Ru(COD)Cl_2$ (305 mg, 0.2 eq.) and finally 5 mL of 3-pentanone were added.

The mixture was stirred at 300 rpm under argon at 90° C. (internal temperature). After 18 hours, the solvent was removed at reduced pressure at 40° C. (10 mbar) and the reaction mixture was analyzed by HPLC and NMR. The yield of the pyrimidine in the crude reaction mixture was 66% based on α-formyl-β-formylaminopropionitrile sodium salt.

Example 8

In the Presence of $ZnBr_2$ 1 g of α-formyl-β-formylaminopropionitrile sodium salt (84%, 5.7 mmol) were placed in a three-necked, round bottom 25 mL flask, fitted with a reflux-condenser, a magnetic stirrer and an argon supply. Acetamidine hydrochloride (670 mg, 6.8 mmol, 1.2 eq.), $ZnBr_2$ (313 mg, 0.24 eq.) and finally 5.4 mL of triethylamine were added.

The mixture was stirred at 300 rpm under argon at 88° C. (internal temperature). After 19 hours, the solvent was removed at reduced pressure at 40° C. (10 mbar) and the reaction mixture was analyzed by HPLC and NMR. The yield was 70% based on α-formyl-β-formylaminopropionitrile sodium salt.

Example 9

In the Presence of $ZnCl_2$ 1 g of α-formyl-β-formylaminopropionitrile sodium salt (77%, 5.2 mmol) were placed in a three-necked, round bottom 25 mL flask, fitted with a reflux-condenser, a magnetic stirrer and an argon supply. Acetamidine acetate (625 mg, 6.2 mmol, 1.2 eq.), $ZnCl_2$ (157 mg, 0.2 eq.) and finally 3 mL of 3-pentanone were added.

The mixture was stirred at 300 rpm under argon at 88° C. (internal temperature). After 16 hours, the solvent was removed at reduced pressure at 40° C. bath temperature and the crude reaction mixture was analyzed by HPLC and NMR. The yield was 62% based on α-formyl-β-formylaminopropionitrile sodium salt.

Example 10

In the Presence of $ZnBr_2$ 1 g of α-formyl-β-formylaminopropionitrile sodium salt (84%, 5.7 mmol) were placed in a three-necked, round bottom 25 mL flask, fitted with a reflux-condenser, a magnetic stirrer and an argon supply. Acetamidine hydrochloride (670 mg, 6.8 mmol, 1.19 eq.), ZnBr$_2$ (661 mg, 0.5 eq.) and finally 1.5 mL of toluene and 4 mL of triethylamine were added.

The mixture was stirred at 300 rpm under argon at 88° C. (internal temperature). After 19 hours, the solvent was removed at reduced pressure at 40° C. bath temperature and the crude reaction mixture was analyzed by HPLC and NMR. The yield was 70% based on α-formyl-β-formylaminopropionitrile sodium salt.

Example 11

In the Presence of ZnCl$_2$ and MgSO$_4$ 2.40 g of α-formyl-β-formylaminopropionitrile (84.4%, 13.68 mmol) were charged in a four-necked flat-bottomed flask, fitted with a reflux-condenser with a water separator and a mechanical stirrer. MgSO$_4$ (1.68 g, 13.68 mmol, 1.0 eq.), acetamidine hydrochloride (1.60 g, 16.41 mmol, 1.20 eq.), ZnCl$_2$ (0.38 g, 0.20 eq.) and finally 40 ml of 3-pentanone were added. The mixture was stirred at 300 rpm and 90° C. for 3 h. After 3 hours, the reaction mixture was dissolved in methanol and the MgSO$_4$ were filtered off. The mixture was concentrated at reduced pressure at 40° C. (10 mbar), and product was analyzed by HPLC. Yield 79% based on α-formyl-β-formylaminopropionitrile sodium salt.

5 experiments were carried out, yield 75-79%.

Example 12

In the Presence of ZnCl$_2$ and Na$_2$SO$_4$ 2.40 g of α-formyl-β-formylaminopropionitrile (84.4%, 13.68 mmol) were charged in a four-necked flat-bottomed flask, fitted with a reflux-condenser with a water separator and a mechanical stirrer. Na$_2$SO$_4$ (1.96 g, 13.68 mmol, 1.0 eq.), acetamidine hydrochloride (1.60 g, 16.41 mmol, 1.20 eq.), ZnCl$_2$ (0.38 g, 0.20 eq.) and finally 40 ml of 3-pentanone were added. The mixture was stirred at 300 rpm and 90° C. for 3 h. After 3 hours, the reaction mixture was dissolved in methanol and the Na$_2$SO$_4$ were filtered off. The mixture was concentrated at reduced pressure at 40° C. (10 mbar), and product was analyzed by HPLC. Yield 78% based on α-formyl-β-formylaminopropionitrile.

Example 13

In the Presence of Zn[N(SO$_2$CF$_3$)$_2$]$_2$ 2.40 g of α-formyl-β-formylaminopropionitrile (84.4%, 13.68 mmol) were charged in a four-necked flat-bottomed flask, fitted with a reflux-condenser with a water separator and a mechanical stirrer. Acetamidine hydrochloride (1.60 g, 16.41 mmol, 1.20 eq.), Zn[N(SO$_2$CF$_3$)$_2$]$_2$ (1.71 g, 0.20 eq.) and finally 40 ml of 3-pentanone were added. The mixture was stirred at 300 rpm and 90° C. for 3 h. After 3 hours, the reaction mixture was dissolved in methanol and the MgSO$_4$ were filtered off. The mixture was concentrated at reduced pressure at 40° C. (10 mbar), and product was analyzed by HPLC. Yield 62% based on α-formyl-β-formylaminopropionitrile.

Example 14

In the Presence of Zn[N(SO$_2$CF$_3$)$_2$]$_2$ and MgSO$_4$ 2.40 g of α-formyl-β-formylaminopropionitrile (84.4%, 13.68 mmol) were charged in a four-necked flat-bottomed flask, fitted with a reflux-condenser with a water separator and a mechanical stirrer. MgSO$_4$ (1.68 g, 13.68 mmol, 1.0 eq.), acetamidine hydrochloride (1.60 g, 16.41 mmol, 1.20 eq.), Zn[N(SO$_2$CF$_3$)$_2$]$_2$ (1.71 g, 0.20 eq.) and finally 40 ml of 3-pentanone were added. The mixture was stirred at 300 rpm and 90° C. for 3 h. After 3 hours, the reaction mixture was dissolved in methanol and the MgSO$_4$ were filtered off. The mixture was concentrated at reduced pressure at 40° C. (10 mbar), and product was analyzed by HPLC. Yield 65% based on α-formyl-β-formylaminopropionitrile.

Example 15

In the Presence of CuCl 10 g of α-formyl-β-formylaminopropionitrile sodium salt (81.7%, 55 mmol) were placed in a three-necked, round bottom 250 mL flask, fitted with a reflux-condenser, a mechanic stirrer and an argon supply. Acetamidine hydrochloride (6.29 g, 65 mmol, 1.17 eq.), CuCl (2.53 g, 0.45 eq.) and finally 70 mL of 3-pentanone were added.

The mixture was stirred at 300 rpm under argon at 88° C. (internal temperature). After 14 hours, the solvent was removed at reduced pressure at 40° C. bath temperature and the crude reaction mixture was analyzed by HPLC and NMR. The yield was 90% based on α-formyl-β-formylaminopropionitrile sodium salt.

Example 16

In the Presence of CuCl and ZnCl$_2$ 4.99 g of α-formyl-β-formylaminopropionitrile sodium salt (81.7%, 27.59 mmol) were placed in a three-necked, round bottom 250 mL flask, fitted with a reflux-condenser, a mechanic stirrer and an argon supply. Acetamidine hydrochloride (3.23 g, 33.14 mmol, 1.2 eq.), CuCl (0.31 g, 0.0.08 eq.), 0.4 g ZnCl$_2$ (0.1 eq) and finally 18 mL of 3-pentanone were added.

The mixture was stirred at 300 rpm under argon at 88° C. (internal temperature). After 14 hours, the solvent was removed at reduced pressure at 40° C. bath temperature and the crude reaction mixture was analyzed by HPLC and NMR. The yield was 74% based on α-formyl-β-formylaminopropionitrile sodium salt.

Example 17

Reaction with Formamidine Hydrochloride 1 g of α-formyl-β-formylaminopropionitrile sodium salt (81.7%, 5.52 mmol) were placed in a three-necked, round bottom 25 mL flask, fitted with a reflux-condenser, a magnetic stirrer and an argon supply. Formamidine hydrochloride (548 mg, 6.6 mmol, 1.21 eq.), ZnCl$_2$ (200 mg, 0.26 eq.) and finally 8 mL of 3-pentanone were added.

The mixture was stirred at 300 rpm under argon at 88° C. (internal temperature). After 6 hours, the solvent was removed at reduced pressure at 40° C. bath temperature and the crude reaction mixture was analyzed by HPLC and NMR. The yield of 4-amino-5-formylaminomethylpyrimidine was 34% based on α-formyl-β-formylaminopropionitrile sodium salt.

Example 18

Reaction with Guanidine Hydrochloride 1 g of α-formyl-β-formylaminopropionitrile sodium salt (81.7%, 5.52 mmol) were placed in a three-necked, round bottom 25 mL flask, fitted with a reflux-condenser, a magnetic stirrer and an argon supply. Guanidine hydrochloride (658 mg, 6.78 mmol, 1.2 eq.), ZnCl$_2$ (263 mg, 0.35 eq.) and finally 8 mL of 3-pentanone were added.

The mixture was stirred at 300 rpm under argon at 88° C. (internal temperature). After 8 hours, the solvent was removed at reduced pressure at 40° C. bath temperature and the crude reaction mixture was analyzed by HPLC and NMR. The yield of 2,4-diamino-5-formylaminomethylpyrimidine was 84% based on α-formyl-β-formylaminopropionitrile sodium salt.

Example 19

Ethyl Acetate as Solvent, in the Presence of ZnCl$_2$ 2.40 g of α-formyl-β-formylaminopropionitrile (84.4%, 13.68 mmol) were charged in a four-necked flat-bottomed flask, fitted with a reflux-condenser with a water separator and a mechanical stirrer. Acetamidine hydrochloride (1.60 g, 16.41 mmol, 1.20 eq.), ZnCl$_2$ (0.38 g, 0.20 eq.) and finally 40 ml of ethyl acetate were added. The mixture was stirred at 300 rpm and 77° C. for 3 h. After 3 hours, the reaction mixture was dissolved in methanol and concentrated at reduced pressure at 40° C. (10 mbar), and product was analyzed by HPLC. Yield 69% based on α-formyl-β-formylaminopropionitrile.

Example 20

Butyl Acetate as Solvent, in the Presence of ZnCl$_2$ 2.40 g of α-formyl-β-formylaminopropionitrile (84.4%, 13.68 mmol) were charged in a four-necked flat-bottomed flask, fitted with a reflux-condenser with a water separator and a mechanical stirrer. Acetamidine hydrochloride (1.60 g, 16.41 mmol, 1.20 eq.), ZnCl$_2$ (0.38 g, 0.20 eq.) and finally 40 ml of butyl acetate were added. The mixture was stirred at 300 rpm and 90° C. for 3 h. After 3 hours, the reaction mixture was dissolved in methanol and concentrated at reduced pressure at 40° C. (10 mbar), and product was analyzed by HPLC. Yield 65% based on α-formyl-β-formylaminopropionitrile.

COMPARATIVE EXAMPLES

Comparative Example 1

Without Lewis Acid 1.67 g of α-formyl-β-formylaminopropionitrile sodium salt (84%, 9.5 mmol) were placed in a three-necked, round bottom 25 mL flask, fitted with a reflux-condenser, a magnetic stirrer and an argon supply. Acetamidine hydrochloride (1.09 g, 11.6 mmol, 1.15 eq.) and finally 2.5 mL of toluene and 6.6 mL of triethylamine were added.

The mixture was stirred at 300 rpm under argon at 88° C. (internal temperature). After 19 hours, the solvent was removed at reduced pressure at 40° C. bath temperature and the crude reaction mixture was analyzed by HPLC and NMR. The yield was 22% based on α-formyl-β-formylaminopropionitrile sodium salt.

Comparative Example 2

Without Lewis Acid 998 mg of α-formyl-β-formylaminopropionitrile sodium salt (84%, 5.7 mmol) were placed in a three-necked, round bottom 25 mL flask, fitted with a reflux-condenser, a magnetic stirrer and an argon supply. Acetamidine hydrochloride (670 mg, 6.8 mmol, 1.19 eq.) and 5.4 mL of 3-pentanone were added.

The mixture was stirred at 300 rpm under argon at 88° C. (internal temperature). After 19 hours, the solvent was removed at reduced pressure at 40° C. bath temperature and the crude reaction mixture was analyzed by HPLC and NMR. The yield was 45% based on α-formyl-β-formylaminopropionitrile sodium salt.

The invention claimed is:

1. A process for the manufacture of a compound of the structure

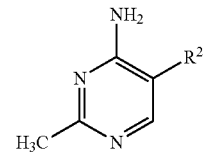

wherein
R$^2$=CH$_2$R$^3$ wherein R$^3$ is H or NHR''' where R'''=formyl
wherein 1 equivalent of an α-formyl-propionitrile salt or an α-formyl-β-formylaminopropionitrile salt is reacted with 0.75 to 2 equivalents of an acetamidine salt in the presence of an additional Lewis acid at the following reaction conditions:
a. a reaction temperature of 65 to 200° C.;
b. a pressure of 1 to 10 bar;
c. a reaction time of 0.5 to 20 hours;
d. a concentration of 1-50 wt.-% α-formylpropionitrile salt or α-formyl-β-formylaminopropionitrile salt in a corresponding solvent;
e. stirring between 100 and 900 rps; and
f. under air or nitrogen or argon or mixtures thereof.
2. Process according to claim 1 wherein the acetamidine salt is a salt of an acid that has a pK$_a$ value below 5.
3. Process according to claim 1 wherein the acetamidine salt is acetamidine hydrochloride, acetamidine hydrobromide and/or acetamidine acetate.
4. Process according to claim 1 wherein the acetamidine salt is acetamidine hydrochloride.
5. Process according to claim 1 wherein the Lewis acids (one or more compounds) are selected from salts of alkaline earth metals, transition metals, poor metals and/or lanthanides.
6. Process according to claim 1 wherein the Lewis acids (one or more compounds) are selected from salts of transition metals.
7. Process according to claim 1 wherein the Lewis acids (one or more compounds) are selected from iron (II)-, cobalt (II)-, ruthenium(II)-, copper(I) and/or zinc(II) salts.
8. Process according to claim 1 wherein the Lewis acids (one or more compounds) are selected from ZnCl$_2$, ZnBr$_2$, Zn((SO$_2$C$_n$F$_{2n+1}$)$_2$)N)$_2$ with n=1 to 8, FeCl$_2$, CoCl$_2$, Ru(COD)Cl$_2$ wherein COD=1,5-cyclooctadiene, CuCl.
9. Process according to claim 1 wherein the Lewis acids (one or more compounds) are selected from CuCl, FeCl$_2$ and ZnCl$_2$.
10. Process according to claim 1 wherein the reaction temperature is 70 to 150° C.
11. Process according to claim 1 wherein the reaction temperature is 80 to 150° C.

12. Process according to claim 1 wherein the reaction temperature is 85 to 120° C.

13. Process according to claim 1 wherein the solvent is selected from solvents or mixtures of solvents which do not have a primary alcohol function.

14. Process according to claim 13 wherein the solvent is selected from hydrocarbons, aromatic compounds, ethers, ketones, esters, carbonates, alcohols, tertiary amines, nitriles, amides, and acetonitrile.

15. Process according to claim 13 wherein the solvent is selected from aromatic compounds, ketones, carbonates, tertiary amines or any mixtures of these solvents.

16. Process according to claim 13 wherein the solvent is 3-pentanone, triethylamine and/or toluene or any mixtures of these solvents.

17. Process according to claim 13 wherein the solvent is 3-pentanone.

18. Process according to claim 13 wherein the solvent is a mixture of 3-pentanone and isopropanol in a volume ratio of from 9:1 to 1:9.

19. Process according to claim 13 wherein the solvent is a mixture of 3-pentanone and isopropanol in a volume ratio of from 8:2 to 2:8.

20. Process according to claim 13 wherein the solvent is a mixture of 3-pentanone and isopropanol in a volume ratio of from 7.5:2.5 to 6:4.

21. Process according to claim 1 wherein the reaction time is in a range of 1 to 10 hours.

22. Process according to claim 1 wherein the reaction time is in a range of 2.5 to 4 hours.

23. Process according to claim 1 wherein the reaction is carried out under protective atmosphere.

* * * * *